(12) United States Patent
Lim et al.

(10) Patent No.: US 7,572,276 B2
(45) Date of Patent: Aug. 11, 2009

(54) MINIMALLY INVASIVE INSTRUMENTS AND METHODS FOR INSERTING IMPLANTS

(75) Inventors: Roy Lim, Germantown, TN (US); Michael C. Sherman, Memphis, TN (US)

(73) Assignee: Warsaw Orthopedic, Inc.

( * ) Notice: Subject to any disclaimer, the term of this patent is extended or adjusted under 35 U.S.C. 154(b) by 1431 days.

(21) Appl. No.: 10/202,918

(22) Filed: Jul. 25, 2002

(65) Prior Publication Data

US 2003/0208203 A1 Nov. 6, 2003

Related U.S. Application Data

(60) Provisional application No. 60/378,569, filed on May 6, 2002.

(51) Int. Cl.
*A61B 17/70* (2006.01)
(52) U.S. Cl. .................... 606/246; 606/86 A; 606/86 B
(58) Field of Classification Search .................. 606/61, 606/99, 104, 60, 253, 256, 279, 280, 281, 606/86 R, 90, 105, 86 A, 86 B
See application file for complete search history.

(56) References Cited

U.S. PATENT DOCUMENTS

| | | | |
|---|---|---|---|
| 5,688,276 A | 11/1997 | Shaffer | |
| 5,735,842 A | 4/1998 | Krueger et al. | |
| 5,788,713 A | 8/1998 | Dubach et al. | |
| 5,910,141 A * | 6/1999 | Morrison et al. | 606/101 |
| 5,947,970 A | 9/1999 | Schmelzeisen et al. | |
| 5,957,927 A | 9/1999 | Magee et al. | |
| 6,036,692 A | 3/2000 | Burel et al. | |
| 6,102,934 A * | 8/2000 | Li | 606/232 |
| 6,113,605 A | 9/2000 | Storer | |
| 6,156,037 A | 12/2000 | LeHuec et al. | |
| 6,530,926 B1 | 3/2003 | Davison | |
| 2001/0021853 A1 | 9/2001 | Heckele et al. | |

FOREIGN PATENT DOCUMENTS

| | | |
|---|---|---|
| DE | 197 54 869 A1 | 6/1999 |
| WO | WO 02/17823 A1 | 3/2002 |

* cited by examiner

*Primary Examiner*—Eduardo C Robert
*Assistant Examiner*—David Comstock

(57) ABSTRACT

Instruments and methods for inserting one or more implants to a surgical site in a patient in a surgical procedure, including minimally invasive surgical procedures are provided. The implant is mountable to the instrument in a reduced profile orientation and after insertion is manipulated with the insertion instrument to the desired orientation.

35 Claims, 11 Drawing Sheets

MINIMALLY INVASIVE INSTRUMENTS AND METHODS FOR INSERTING IMPLANTS

CROSS-REFERENCE TO RELATED APPLICATION

The present application claims the benefit of the filing date of Provisional Application No. 60/378,569, filed on May 6, 2002.

BACKGROUND

Surgery for a patient can be painful and traumatic, particularly in the affected area of the patient's body. For example, the dissection and retraction required to access the surgical site in the patient can cause trauma to the dissected and retracted tissue as well as to the surrounding tissue. The tissue must heal properly for satisfactory patient recovery, and scar tissue can even result when the affected tissue heals.

Tissue dissection and retraction can be required to insert an implant in a patient to a surgical site. Some procedures involve mounting the implant on an instrument that holds the implant as it is inserted to the surgical site. To accommodate implant insertion, sufficient muscle and vasculature and other tissue must be dissected and retracted to allow passage of the implant therethrough.

There remains a need for instruments and methods that can be employed for implant insertion that minimize or facilitate the minimization of tissue dissection and retraction and exposure of the patient's body to the surgical procedure. The present invention is directed to meeting these needs, among others.

SUMMARY

The invention relates instruments and methods for inserting one or more implants to a surgical site in a patient in a surgical procedure, including minimally invasive surgical procedures.

According to one aspect, a system is provided that includes an implant positionable adjacent a surgical space associated with a spinal column of a patient and an insertion instrument. The insertion instrument includes an articulating implant holder adjacent a distal end thereof releasably engageable to the implant. The implant is moveable with the implant holder between a reduced profile orientation relative to the insertion instrument and an increased profile orientation relative to the insertion instrument. The implant holder is adapted to release the implant from the implant holder in the increased profile orientation when the implant is unconstrained relative to the surgical space.

According to another aspect, there is provided a system that includes an implant positionable adjacent a surgical space associated with a spinal column of a patient and an insertion instrument. The insertion instrument includes an articulating implant holder at a distal end thereof releasably engageable to the implant. The implant holder is movably biased to a first position where the implant has a reduced profile orientation relative to the insertion instrument. The implant holder is moveable from the biased first position to a second position where the implant has an increased profile relative to the insertion instrument.

According to another aspect, a system is provided that includes an elongated implant having a first end and a second end and a central axis extending therebetween. The system also includes a control system, a connector system having a proximal end portion adjacent the control system and a distal end portion. An implant holder is positioned adjacent the distal end portion of the connector system and is releasably engageable with the implant between its first and second ends. The implant holder is movable between a reduced profile orientation where the central axis of the implant extends generally along a longitudinal axis of the connector system and a desired orientation where the central axis of the implant extends generally transverse to the longitudinal axis of the implant.

According to one aspect, there is provided a system that includes a bone plate having a receptacle therein and an insertion instrument. The insertion instrument includes an articulatable implant holder adjacent a distal end thereof releasably engageable in the receptacle of the bone plate. The implant holder is movable from a first position where the bone plate has a reduced profile orientation relative to the insertion instrument for insertion of the bone plate to a surgical space in a patient to a second position where the bone plate has an enlarged profile relative to the insertion instrument for engagement of the bone plate at the surgical space.

According to another aspect, a system is provided that includes an elongated spinal rod and an insertion instrument. The insertion instrument includes an articulatable implant holder adjacent a distal end thereof releasably clampable about the spinal rod. The implant holder is movable from a first position where the spinal rod has a reduced profile orientation relative to the insertion instrument for insertion of the spinal rod to a surgical space in a patient to a second position where the spinal rod has an enlarged profile relative to the insertion instrument for engagement of the spinal rod at the surgical space.

According to another aspect, an insertion instrument for positioning an implant at a surgical site in a patient is provided. The insertion instrument includes a control system, a connector system extending distally from the control system, and an implant holder adjacent a distal end of the connector system. There is also included a locking system associated with the implant holder that is remotely actuatable between an unlocked position where the implant holder is released from the implant to a locked position where the implant holder is engaged with the implant. A manipulator system associated with the moves the implant holder between a first position where the implant has a reduced profile orientation for insertion to the surgical site and a second position providing an enlarged profile.

According to another aspect, there is provide an insertion instrument for positioning an implant at a surgical space in a patient. The insertion instrument includes a handle assembly and a shaft assembly extending distally from the handle assembly. The shaft assembly includes a first shaft axially translatable relative to a second shaft. An implant holder is positioned adjacent a distal end of one of the first and second shafts. The implant holder is releasably engageable with the implant. The implant holder has a reduced profile orientation for insertion of the implant to the surgical site and is movable to an enlarged profile orientation for positioning the implant at the surgical space upon axial translation of the first and second shafts relative to one another.

According to one aspect, a method for positioning a bone plate along a spinal column of a patient includes accessing the spinal column through a minimally invasive access path through skin and tissue of the patient; securing the bone plate on an insertion instrument with a longitudinal axis of the bone plate extending generally in the direction of the path through the skin and tissue; positioning the bone plate through the path with the insertion instrument to a location adjacent the spinal column; and remotely manipulating the bone plate relative to the insertion instrument to a desired orientation along the spinal column.

According to another aspect, an insertion instrument for positioning an implant at a surgical space in a patient is provided. The insertion instrument includes a handle assembly and a shaft assembly extending distally from said handle assembly. An implant holder is positioned adjacent a distal end of the shaft assembly. The implant holder is releasably engageable to the implant and is moveable between a reduced profile orientation relative to the shaft assembly and an increased profile orientation relative to the shaft assembly. The implant holder is adapted to release the implant when the implant is positioned adjacent to and substantially unconstrained in the surgical space.

According to another aspect, a method for positioning a spinal rod along a spinal column of a patient includes accessing the spinal column through a minimally invasive access path through skin and tissue of the patient; securing the spinal rod on an insertion instrument with a longitudinal axis of the spinal rod extending generally in the direction of the path through the skin and tissue; positioning the spinal rod through the path with the insertion instrument to a location adjacent the spinal column; and remotely manipulating the spinal rod relative to the insertion instrument to a desired orientation along the spinal column.

These and other aspects of the invention will also be apparent from the following description of the illustrated embodiments.

DESCRIPTION OF THE ILLUSTRATED EMBODIMENTS

Figure 1:
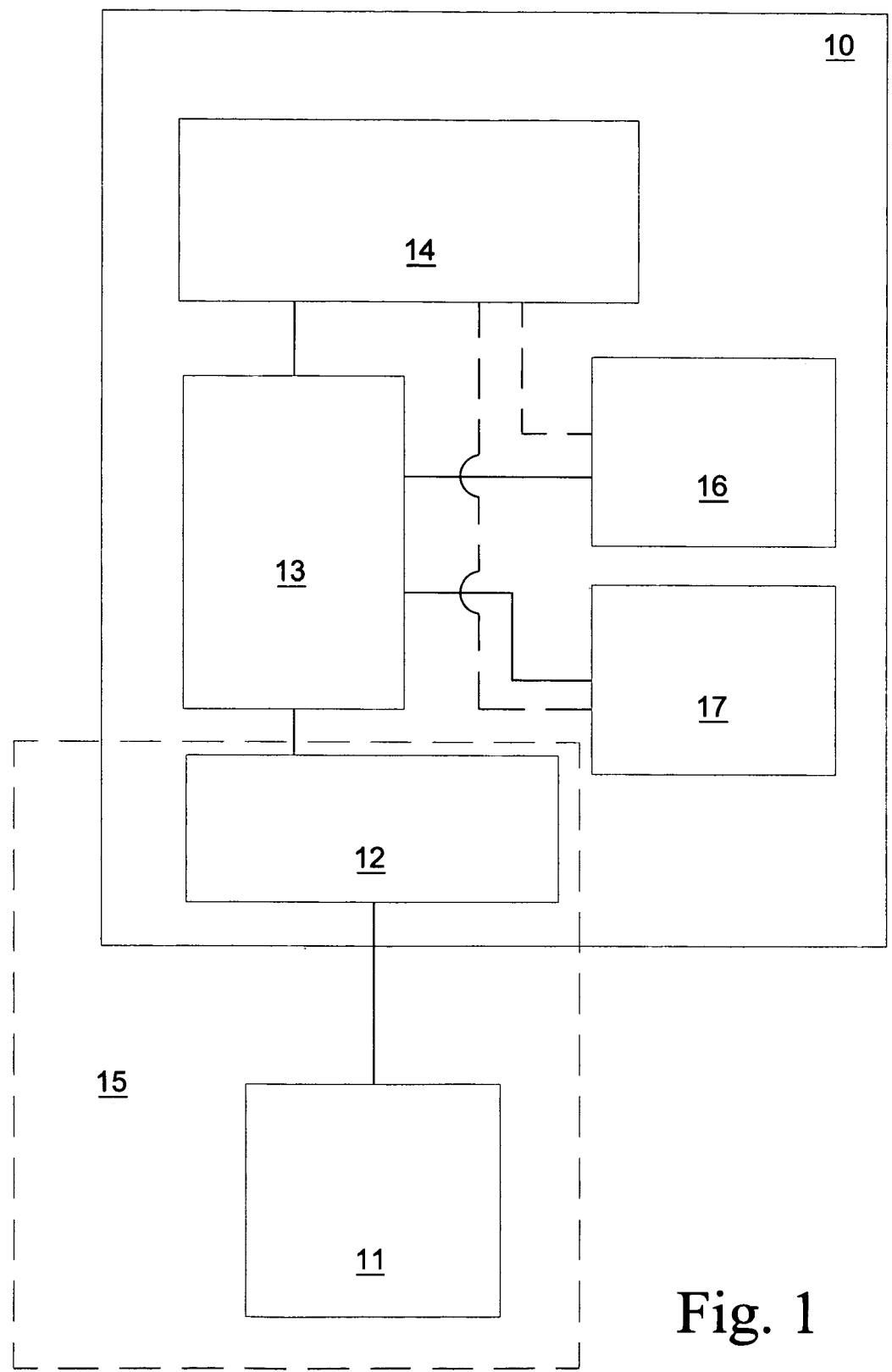
FIG. 1 is a diagrammatic illustration of an implant insertion system.

For the purposes of promoting an understanding of the principles of the invention, reference will now be made to the embodiment illustrated in the drawings and specific language will be used to describe the same. It will nevertheless be understood that no limitation of the scope of the invention is thereby intended. Any such alterations and further modifications in the illustrated device and any such further applications of the principles of the invention as illustrated therein are contemplated as would normally occur to one skilled in the art to which the invention relates.

Referring to FIG. 1, embodiments of an implant insertion instrument 10 for remotely holding, manipulating and releasing a surgical implant 11 include an articulating implant holder 12 spaced apart along a connector system 13 from a control system 14. Control system 14 remotely allows direct positioning of implant holder 12 within a surgical space 15, such as within a body cavity accessed in an open or minimally-invasive fashion. Additionally, insertion instrument 10 includes a manipulator system 16 for adjusting an orientation of implant holder 12, and hence implant 11, relative to the insertion instrument. Also, insertion instrument 10 may include a lock system 17 for releasably securing implant 11 relative to the insertion instrument. Manipulator system 16 and lock system 17 may be remotely positioned relative to implant holder 12, and may form a portion of control system 14.

In operation, insertion instrument 10 secures implant 11 on implant holder 12, such as through adjusting lock system 17 into a locked state, and control system 14 directs insertion of the implant into surgical space 15. At least upon the initial insertion, manipulator system 16 positions implant holder 12 and implant 11 in a first orientation, which may be a rigidly fixed position. At least after the initial insertion or upon entry into surgical space 15, manipulator system 16 may reposition implant holder 12 and implant 11 into at least a second orientation, which may be a rigidly fixed position, that facilitates fixation of the implant within the surgical space. Insertion instrument 10 is disconnected from implant 11 by adjusting lock system 17 into an unlocked state, and the insertion instrument may be removed from surgical space 15.

Surgical implant 11 may include any implantable device. Suitable examples of surgical implant 11 include a plate, a rod, a bone screw, a multi-axial bone screw, a fusion member, an artificial disc implant, an articulation member, an anchor, a staple, an interbody fusion device, and a tissue scaffold.

Implant holder 12 includes a structure configured to hold implant 11. Implant holder 12 may include expanding mechanisms, contracting mechanism, grasping mechanisms, screw mechanisms, wedge structures, dove-tail structures, and ball-detent mechanisms, for example. Implant holder 12 may be integral with or separate from connector system 13 and also locking system 17.

Connector system 13 includes a member connectable between manipulator system 16 and implant holder 12. Additionally, connector system 13 may be rigid, flexible or a combination of both. Connector system 13 may include tubular elements, rod-like elements, linkages, elastically-deformable members, and articulating connectors, for example.

Control system 14 includes a member, such as a handle, for controlling the depth, angular orientation and rotational orientation of implant holder 12. Other suitable examples of control system 14 include t-bars, pistol-grips, hooks, circular finger controls, co-axial shafts, and side-by-side shafts.

Manipulator system 16 includes any device or mechanism capable of adjusting the position or orientation of implant holder 12 and/or implant 11 relative to insertion instrument 10. Manipulator system 16 may include linkage systems, wire systems, gear systems, flexible adjustment systems, etc. Manipulator system 16 may include linear and/or rotationally moving elements. Manipulation system 16 may rigidly fix the position of implant holder 12 relative to insertion instrument 10 throughout and/or only at predetermined portions along a range of orientations relative to insertion instrument 10.

Lock system 17 includes any device or mechanism capable of releasably securing implant 11 to insertion instrument 10. Suitable examples of lock system 17 include force-fit or wedge-type locking mechanisms, pivoting lock mechanisms, rotating lock mechanisms, geared lock mechanisms, etc. Lock system 17 may rigidly secure implant 11 to implant holder 12 throughout and/or only at predetermined portions along a range of orientations of the implant holder relative to insertion instrument 10.

Figure 2:
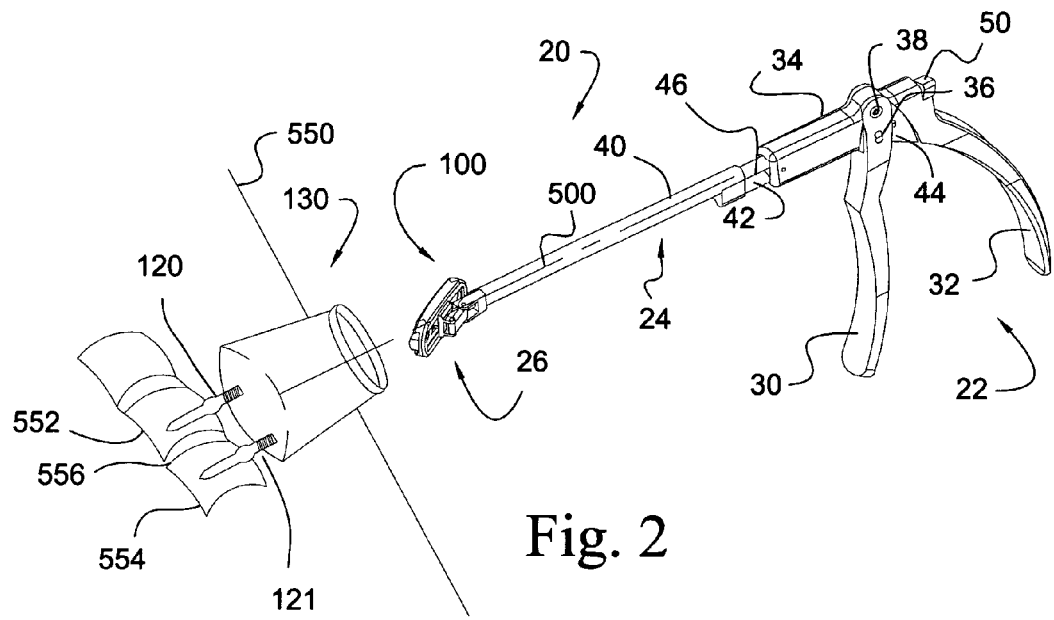
FIG. 2 is a perspective view showing an insertion instrument with an implant engaged thereto in a reduced profile orientation before insertion of the implant to a surgical space in a patient.
Figure 3:
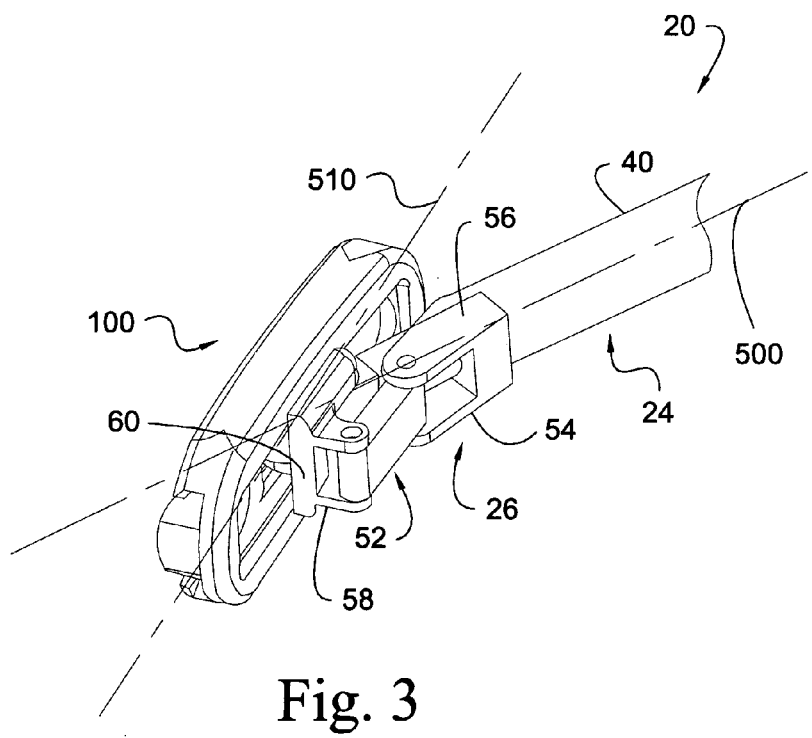
FIG. 3 is an enlarged perspective view of the distal end of the insertion instrument and the implant of FIG. 2.

Referring to FIGS. 2 and 3, insertion instrument 20 will be described with specific reference to an implant 100 in the form of a plate attachable to anchors 120, 121 engaged to vertebrae 552 and 554, respectively, of the spinal column of the patient. Insertion instrument 20 has a control system that includes a proximal handle assembly 22, and connector and manipulator systems that include a shaft assembly 24 extending distally from handle assembly 22. Insertion instrument 20 further includes an implant holder 26 at the distal end of shaft assembly 24. Implant 100 is releasably mountable to implant holder 26.

In FIG. 2, implant 100 may be rigidly mounted on insertion instrument 20 in a first position having a low profile orientation for insertion of implant 100 to a surgical space in a patient through pathway 130. In the reduced profile orientation, longitudinal axis 510 of implant 100 may be at any angle from 0 degrees to less than 90 degrees relative to longitudinal axis 500 of shaft assembly 24. For example, axis 510 may be obliquely oriented to and in the general direction of longitudinal axis 500 of shaft assembly 24. In the illustrated embodiment, implant 100 has a curved central axis 510, although implants with linear central axes are also contemplated. Other embodiments contemplate that central axis 510 of implant 100 could be coaxial with or parallel to longitudinal axis 500 in the reduced profile orientation. This reduced profile orientation minimizes the footprint of implant 100 relative to insertion instrument 20 and transverse to its insertion path as implant 100 is inserted through pathway 130 to the surgical space. After insertion through pathway 130, implant 100 is moved from its reduced profile insertion orientation to a desired orientation relative to anchors 120, 121 for engagement of implant 100 thereto.

Figure 4:
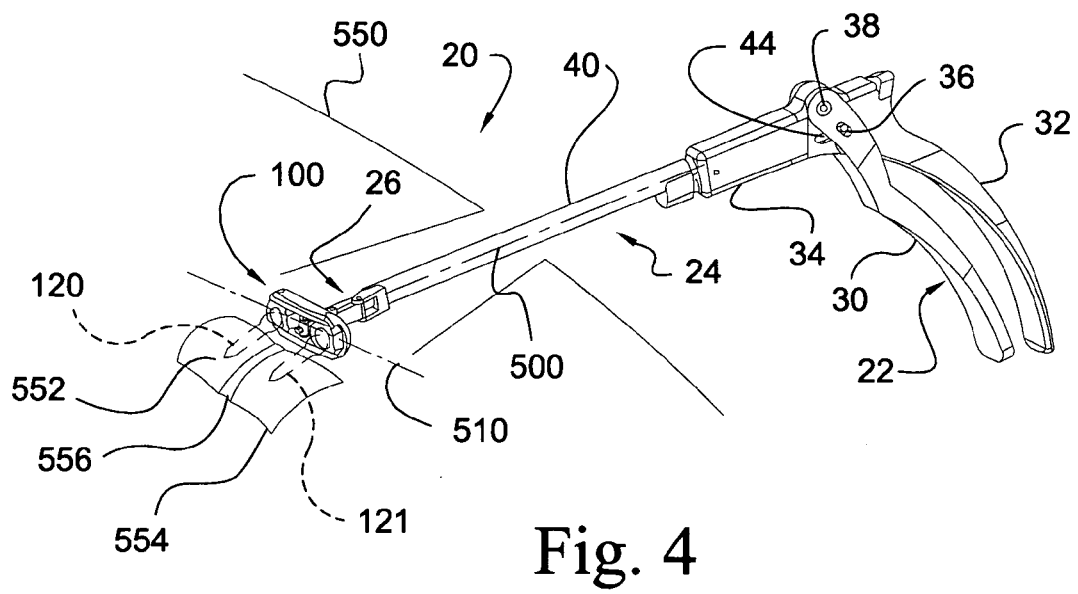
FIG. 4 is a perspective view showing the insertion instrument with the implant engaged thereto in an actuated orientation after insertion of the implant to the surgical space in the patient.
Figure 5:
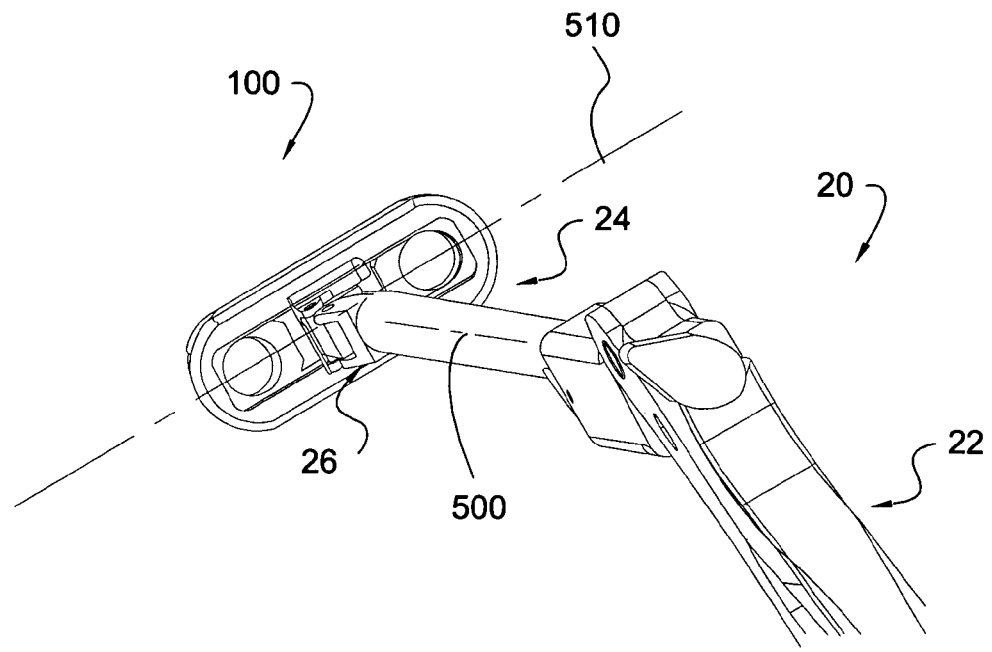
FIG. 5 is a perspective view looking at the proximal end of the insertion instrument and the implant with the thumb lever in a locked position.
Figure 6:
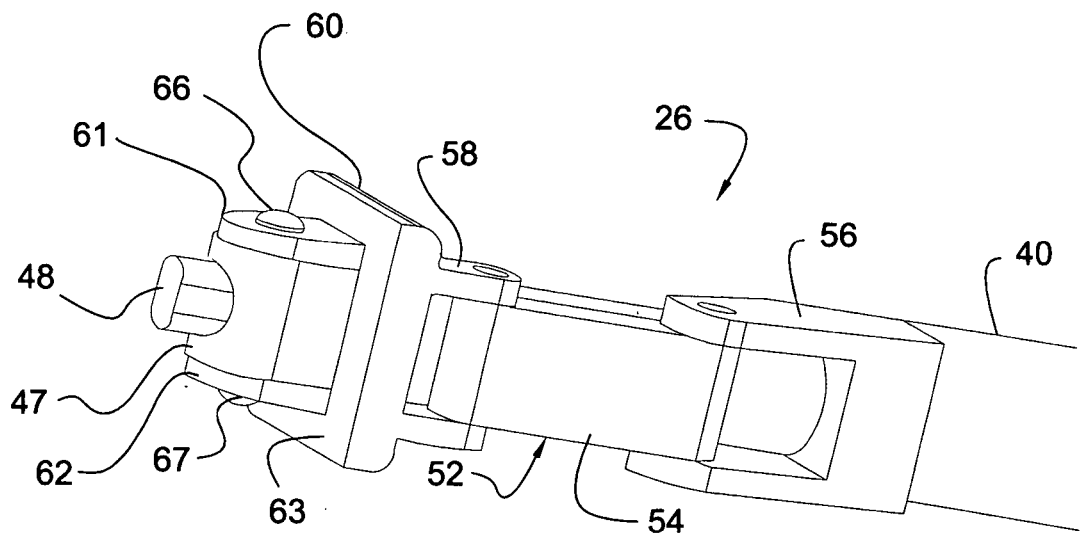
FIG. 6 is an enlarged perspective view of the distal end portion of the insertion instrument the thumb lever in a locked position.

In FIGS. 4 and 5, handle assembly 22 is manipulated by the surgeon to actuate implant holder 26 through shaft assembly 24 to move implant 100 to a second position or orientation with respect to insertion instrument 20, and also with respect to anchors 120, 121. Implant 100 may be rigidly fixed to implant holder 26 throughout the movement from the first position to the second position. In the second, actuated orientation, longitudinal axis 510 of implant 100 extends more transversely to longitudinal axis 500 of shaft assembly 24 than when in the reduced profile orientation. It is contemplated that the actuated implant 100 is placed in the desired orientation for engagement of implant 100 with anchors 120, 121. In the actuated orientation, the footprint of implant 100 in the implant insertion direction through pathway 130 can be greater than the opening of pathway 130 at least adjacent skin level 550. Thus, the amount of tissue dissection and retraction required to accommodate insertion of implant 100 to the surgical space is minimized.

With implant 100 positioned in the desired position within the operative space, such as relative to anchors 120, 121, insertion instrument 20 can be detached from implant 100 and removed from pathway 130. Handle assembly 22 may include a remote lock mechanism for remotely securing and releasing implant 100 relative to instrument 20. Further instruments and implants such as set screws, nuts, sutures, anchors or other fastening elements can be inserted through pathway 130 to secure implant 100 at the surgical space.

In the illustrated embodiment, the surgical space is associated with the spine of the patient, and implant 100 is a plate attachable to anchors 120 and 121 engaged to vertebrae 552 and 554, respectively, on each either side of disc space 556. Pathway 130 is a retractor sleeve that provides a protected working channel through skin 550 to the surgical space. The illustrated retractor sleeve is inserted in a cylindrical configuration through skin 550 and thereafter expandable to a frusto-conically shaped configuration to provide access to each of the anchors 120, 121 at the distal end thereof through the working channel. The opening size of pathway 130 at skin 550 and to the surgical space is minimized to reduce the incision size and trauma to the surrounding tissue.

Pathway 130 can also be formed by non-expandable retractor sleeves or guide sleeve, or by a micro-incision or open incision without a retractor sleeve, or by tissue retractors that do not form a sleeve. It is also contemplated that the tissue through pathway 130 can be sequentially dilated to form the desired pathway size while minimizing trauma to the adjacent tissue. Endoscopic, microscopic or other viewing instruments and techniques are contemplated for viewing the surgical space.

One embodiment of the invention contemplates that implant 100 is a bone plate. Other embodiments contemplated other implants, such as a rod, strut, linking member, bone fusion member, articulating member, or other implant in which it is desirable to minimize its profile for insertion through a pathway and thereafter alter its orientation after insertion through the pathway. Anchors 120, 121 can be bone screws or bolts with proximal ends adapted to receive implant 100 thereover or therein. Anchors 120, 121 can also be bone screws that are multi-axial or uni-axial in form. Anchors 120, 121 can also be, for example, in the form of hooks, staples, spikes, clamps, interbody fusion devices, interbody implants, intravertebral fusion device, or other intravertebral or intervertebral implant. The proximal ends of anchors 120, 121 to which implant 100 is engaged can be a threaded or unthreaded stem, U-shaped yoke or other receptacle or bearing surface configured for engagement with an implant 100. It is further contemplated that implant 100 can be placed against or adjacent to the bone or tissue to which it is to be engaged, and then engaged thereto with anchors positioned after implant placement.

One specific application contemplates positioning the implant at a surgical space on or near the spine. Any one of a number of approaches to the spine are contemplated, including anterior, posterior, lateral, poster-lateral, antero-lateral approaches, for example. The insertion instrument can be employed in endoscopic, laparoscopic, thorascopic or other minimally invasive or open procedures. The implant can be attached to bony portions of the spine, including, for example, the vertebral bodies, vertebral endplates, pedicles, facet joints, or the various processes of the spine. Applications in areas other than spinal surgery are also contemplated.

Referring further to FIGS. 2-6, handle assembly 22 includes distal handle portion 30 pivotally coupled via a pin 38 to an extension 34 of a proximal handle portion 32. Shaft assembly 24 includes an outer shaft 40 extending along axis 500 between handle assembly 22 and implant holder 26. Distal handle portion 30 is engaged to an outer shaft extension 42 (FIG. 2.) Outer shaft extension 42 extends proximally from outer shaft 40 through extension 34, where it is coupled with distal handle portion 30 with pin 36. An intermediate shaft 46 is coupled to and extends proximally from extension 34 of proximal handle portion 32. Distal handle portion 30 and proximal handle portion 32 can be biased via a spring or the like to the position shown in FIG. 2 so that outer shaft 40 is fully extended distally relative to intermediate shaft 46. As distal handle portion 30 is moved toward proximal handle portion 32, pin 36 moves proximally in groove 44 of extension 34, axially translating outer shaft 40 proximally relative to intermediate shaft 46 and pivoting the implant holder.

Figure 7:
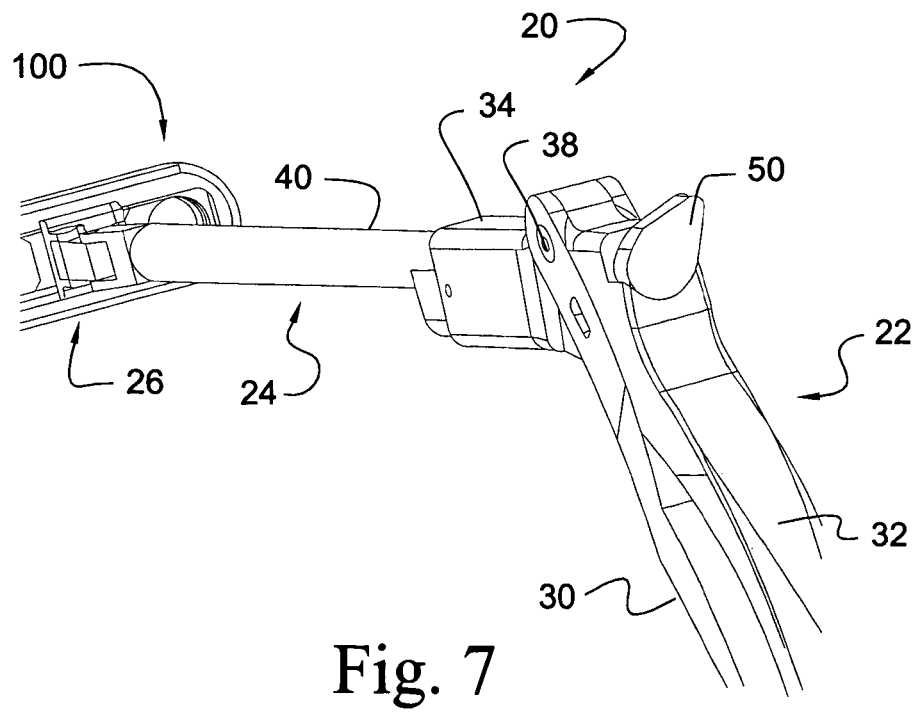
FIG. 7 is a perspective view looking at the proximal end of the insertion instrument and implant with the thumb lever in an unlocked position.
Figure 8:
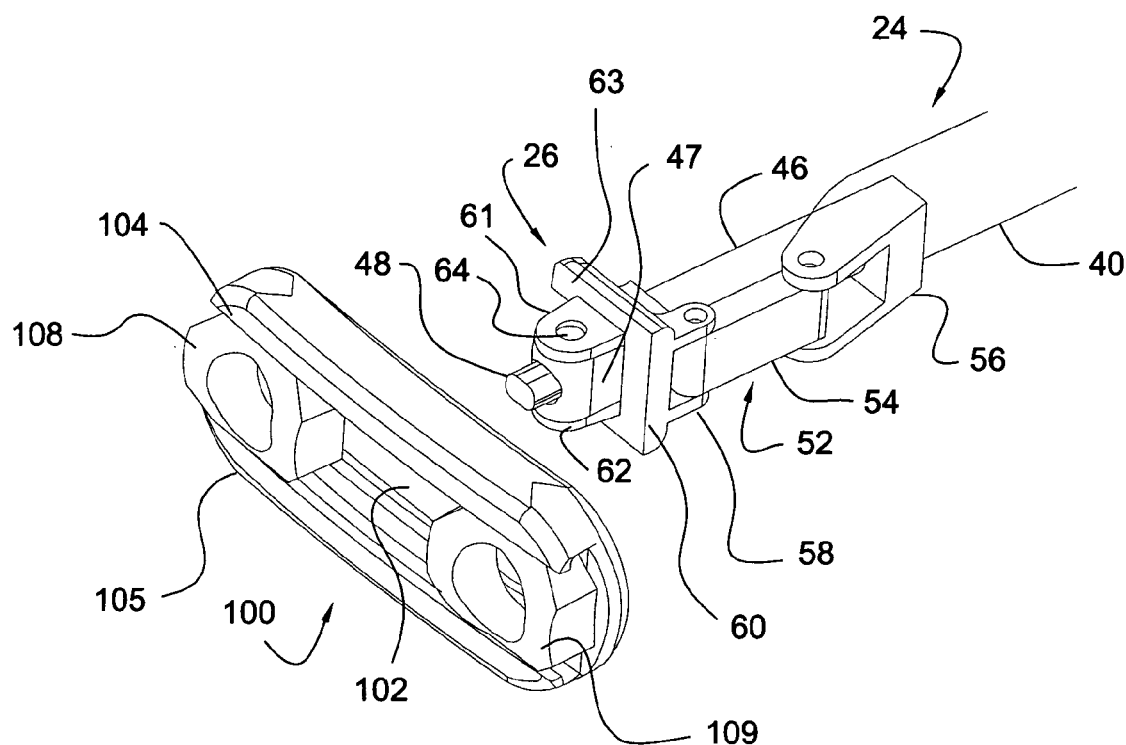
FIG. 8 is a perspective view of the distal end portion of the insertion instrument of FIG. 2 in an unlocked position and uncoupled from the implant of FIG. 2.
Figure 9:
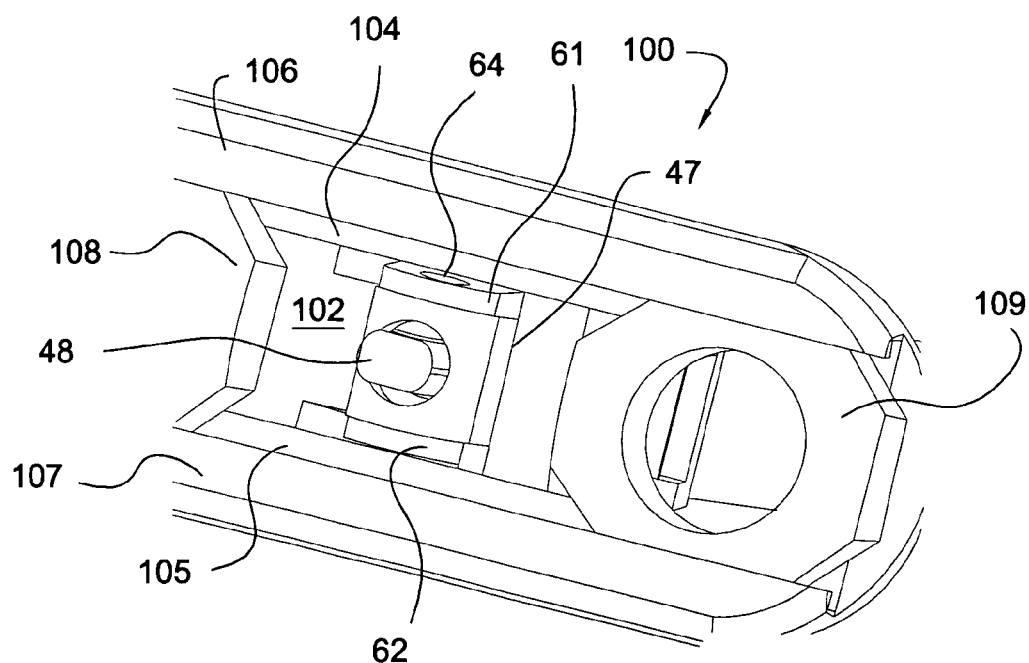
FIG. 9 is a view of the bottom of the implant with the distal end portion of the insertion instrument positioned in a receptacle of the implant and unengaged thereto.

Referring to FIGS. 5-10, one embodiment of a lock system associated with insertion instrument 20 includes a cam member 48 extending through intermediate shaft 44, and a lever 50 at a proximal end of intermediate shaft 44. Lever 50 is manipulated by the surgeon to move cam member 48 between an unlocked position, as shown in FIGS. 7, 8 and 9, and a locked position, as shown in FIGS. 2, 4, 5, 6 and 10. As discussed further below, cam member 48 is engageable with engagement members that couple the implant to implant holder 26 of insertion instrument 20.

A linkage mechanism 52 is coupled between the distal end of outer shaft 40 and implant holder 26. Linkage mechanism 52 includes a link 54 pivotally coupled to a bracket 56 extending laterally from the distal end of outer shaft 40. The opposite end of link 54 is pivotally coupled to a bracket 58 of implant holder 26. Implant holder 26 further includes an articulating member 60 pivotally mounted to a mounting portion 47 at the distal end of intermediate shaft 46. Cam member 48 extends through intermediate shaft 46, including mounting portion 47. A pair of fingers 61, 62 extend distally from articulating member 60, forming a distal lip 63 therewith. Fingers 61, 62 each include a hole 64 (only one shown) therethrough.

A pair of engagement members 66, 67 are movably captured in mounting portion 47 of intermediate shaft 46. With cam member 48 in the unlocked position, engagement members 66, 67 can move into mounting portion 47 and recess below the outer surfaces of fingers 61, 62, as shown in FIGS. 7-9. When cam member 48 is moved to its locked position with lever 50, cam member 48 contacts engagement members 66, 67 and forces each outwardly relative to mounting portion 47 and through the aligned holes 64 of fingers 61, 62, as shown in FIGS. 4, 5, 6 and 10. Engagement members 66, 67 may have a spherically shaped surface extending from fingers 61, 62 to allow the implant to force the engagement members into the recessed position to facilitate mounting, dismounting and locking of the implant. Engagement members 66, 67 can be provided with an enlarged shoulder (not shown) within mounting portion 47 that abuts mounting portion 47 when engagement members 66, 67 extend from fingers 61, 62 to retain engagement members 66, 67 therein.

Figure 10:
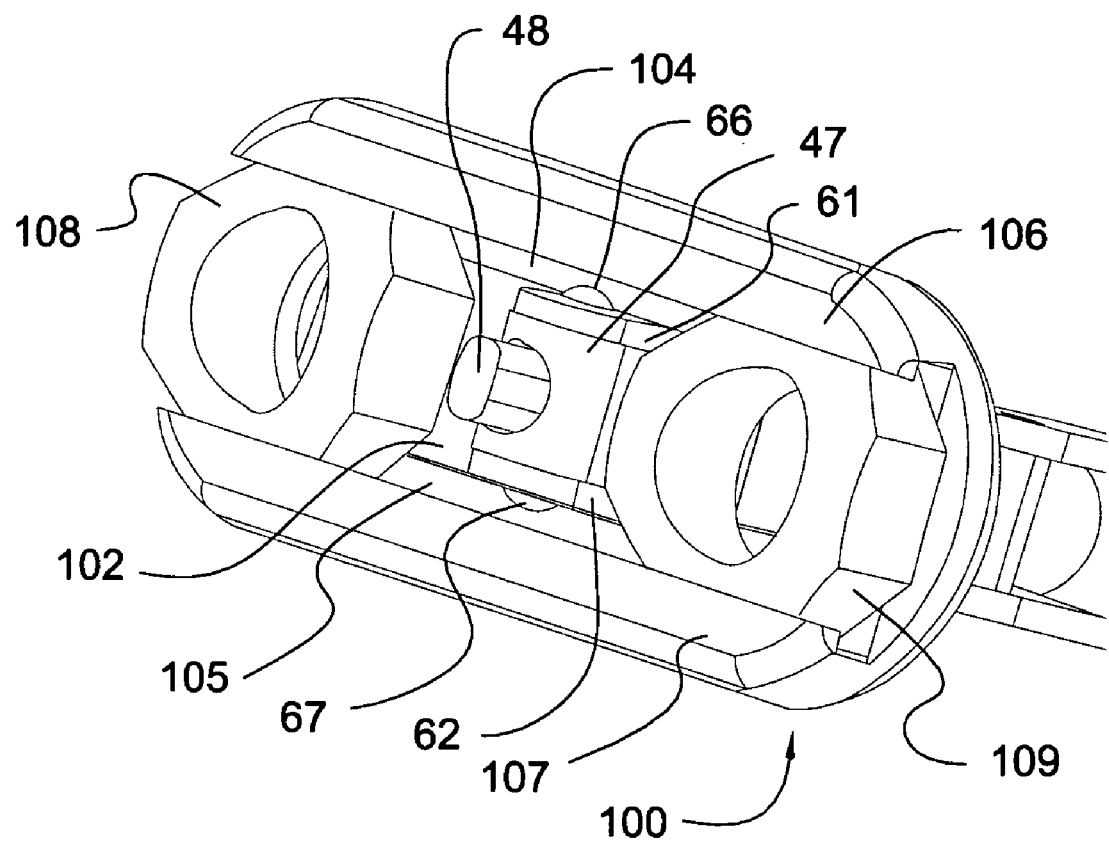
FIG. 10 is a view of the bottom of the implant with the distal end portion of the insertion instrument positioned therein and engaged thereto.

With reference to FIGS. 8-10, one embodiment of a method of mounting implant 100 on implant holder 26 of insertion instrument 20 will be described. Implant 100 may include a receptacle 102 defined by a pair of upper rails 104, 105 and a pair of lower rails 106, 107. Slidably positioned between rails 104, 105 and rails 106, 107 are slide washers 108, 109. Washers 108, 109 each have a hole therethrough sized to receive an anchor to couple implant 100 to a bony segment, such as adjacent vertebrae 552 and 554. Washers 108, 109 can be slidably adjusted along the upper and lower rails and positioned at the desired location in the plate based on the anchor spacing. It is further contemplated that implant 100 can include more than two washers 108, 109. It should be understood that implant 100 can be any type of plate or implant which has a receptacle sized to receive implant holder 26. Other embodiments contemplate that implant 100 does not include a receptacle, but rather the insertion instrument is coupled to the implant via other means. For example, the implant holder could be clamped around the implant or a portion of the implant, or the implant holder could be fastened to the implant.

As shown in FIG. 8, implant 100 is mounted to insertion instrument 20 by inserting holding portion 26 into receptacle 102 of the implant. To mount implant 100 on holding portion 26, it may be desirable for insertion instrument to be placed in its actuated condition. Thus, distal handle portion 30 can be moved toward proximal handle portion 32 to translate outer shaft 40 proximally along intermediate shaft 46. This causes linkage mechanism 52 to pivot so that link 54 extends along intermediate shaft 46, pulling the side of articulating member 60 coupled to link 52 proximally as well. To insert implant holder 26 into receptacle 102, lever 50 is moved to its unlocked position (FIG. 7) thereby moving cam member 48 to its unlocked position, allowing engagement members 66, 67 to move inwardly into mounting portion 47 and below the outer surface of fingers 61, 62. Fingers 61, 62 are inserted into receptacle 102, as shown in FIG. 9, to a depth that allows engagement members 66, 67 to contact implant 100, such as until lip 63 is positioned adjacent the upper or proximal surface of implant 100.

Once fingers 61, 62 are inserted in receptacle 102 of implant 100, lever 50 is moved to its locked position, thus rotating cam member 48 and pushing engagement members 66, 67 out respective ones of the holes 64, as shown in FIG. 10. The outwardly biased engagement members 66, 67 form an expansion lock with the interior portion of implant 100, such as by contacting the underside of upper rails 104, 105 to prevent implant 100 from being removed from implant holder 26. Once implant 100 is engaged to insertion instrument 100, distal handle portion 30 of handle assembly 22 can be released so that outer shaft 40 moves distally along intermediate shaft 46 to its unactuated position. In the unactuated position, link 54 pushes the side of articulating member 60 to which it is pivotally attached distally, causing articulating member 60 to pivot about mounting portion 47. The pivoting of articulating member 60 also pivots implant 100 so that its central axis 510 extends at any angle from 0 degrees to less than 90 degrees relative to axis 500, such as extending obliquely to or in the general direction of longitudinal axis 500 of insertion instrument 20, as shown in FIGS. 2 and 3.

In its unactuated position, implant 100 has a reduced profile such that its footprint transverse to longitudinal axis 500 is minimized. In this position, implant 100 can be inserted in a minimally invasive access pathway to the surgical site. Once inserted through the pathway to the surgical site, distal handle portion 30 of handle assembly 22 is moved toward proximal handle portion 32, translating outer shaft 40 proximally along intermediate shaft 46. This in turn actuates linkage mechanism 52, which pulls the side of articulating member 60 to which it is attached proximally. This pivots articulating member 60 about mounting portion 47 to position implant 100 in its desired orientation relative to anchors 120, 121, as shown in FIGS. 4 and 5, so that implant 10 can be engaged thereto. Once implant 100 is in its desired position at the surgical site, lever 50 can be moved to its unlocked position, which remotely rotates cam member 48 to its orientation in FIGS. 8 and 9. Engagement members 66, 67 can then easily slide through holes 64 and into mounting portion 47 so that implant holder 26 can be withdrawn from receptacle 102. Implant 100 can be released in the surgical space in a substantially unconstrained condition, and thereafter constrained or secured as desired. Insertion instrument 20 could also release implant 100 in a constrained condition provided by substantial contact between implant 100 and the anatomy, bone fastener or the like positioned in the surgical space.

Referring now to FIGS. 11-19 there is illustrated another embodiment insertion instrument designated at 220. Insertion instrument 220 includes components corresponding to those of insertion instrument 20 discussed above, and like components between instruments 20 and 220 are designated with the same reference numerals. Insertion instrument 220 includes a handle assembly 22, a shaft assembly 24 and an implant holder 76 at the distal end of shaft assembly 24. Implant holder 76 is configured to clamp or grip surfaces of the implant. In the illustrated embodiment, implant 200 is in the form of a spinal rod gripped by implant holder 76. Other embodiments contemplate other types of implants, such as plates, fusion members, articulating members, or anchors for example, that could be gripped by implant holder 76.

Figure 11:
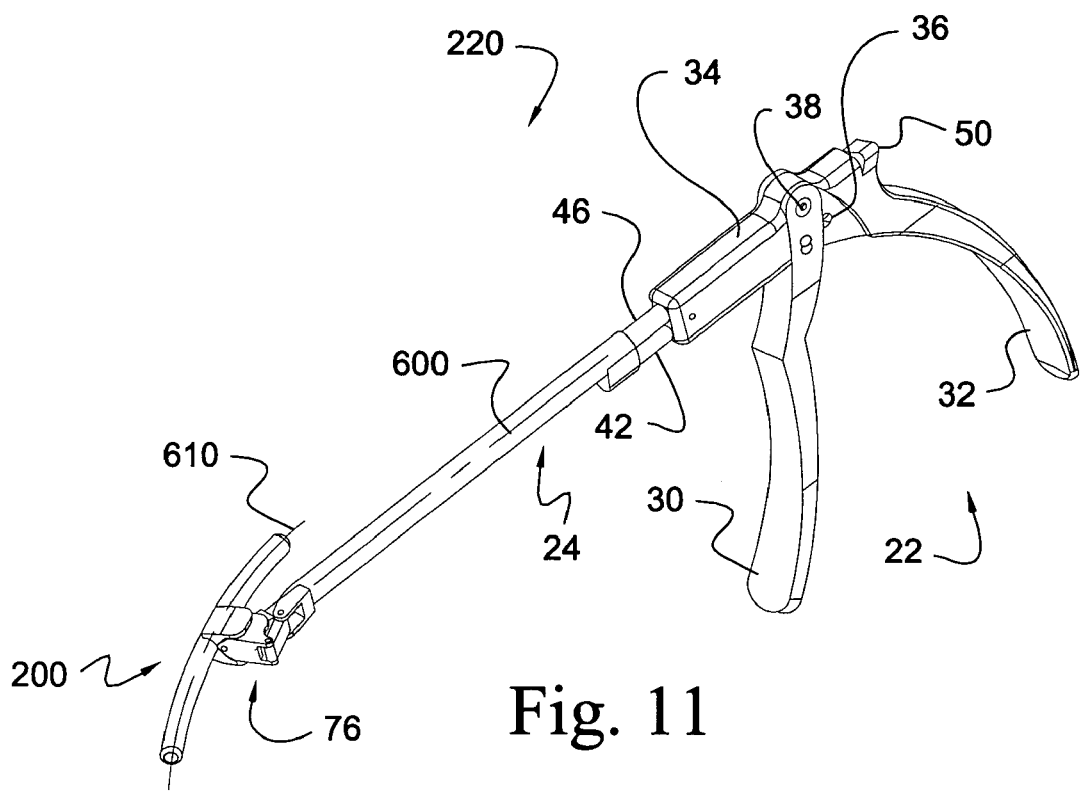
FIG. 11 is a perspective view showing another embodiment insertion instrument with an implant engaged thereto in a reduced profile orientation before insertion of the implant to a surgical space in a patient.

Implant 200 is releasably mounted to insertion instrument 220 with implant holder 76. In FIG. 11, implant 200 is positioned on insertion instrument 220 in a first position having a reduced profile orientation for insertion to a surgical space in a patient through a pathway, as discussed above. In the reduced profile orientation, longitudinal axis 610 of implant 200 extends at any angle, except perpendicular, such as obliquely to and in the general direction of longitudinal axis 500 of shaft assembly 24. This minimizes the footprint of implant 200 relative to insertion instrument 220 for insertion implant 200 through the pathway. In the illustrated embodiment, implant 200 has a curved central axis 510, although implants with linear central axes are also contemplated. Other embodiments contemplate that central axis 610 of implant 200 could be coaxial with or parallel to longitudinal axis 600 in the reduced profile orientation.

Figure 12:
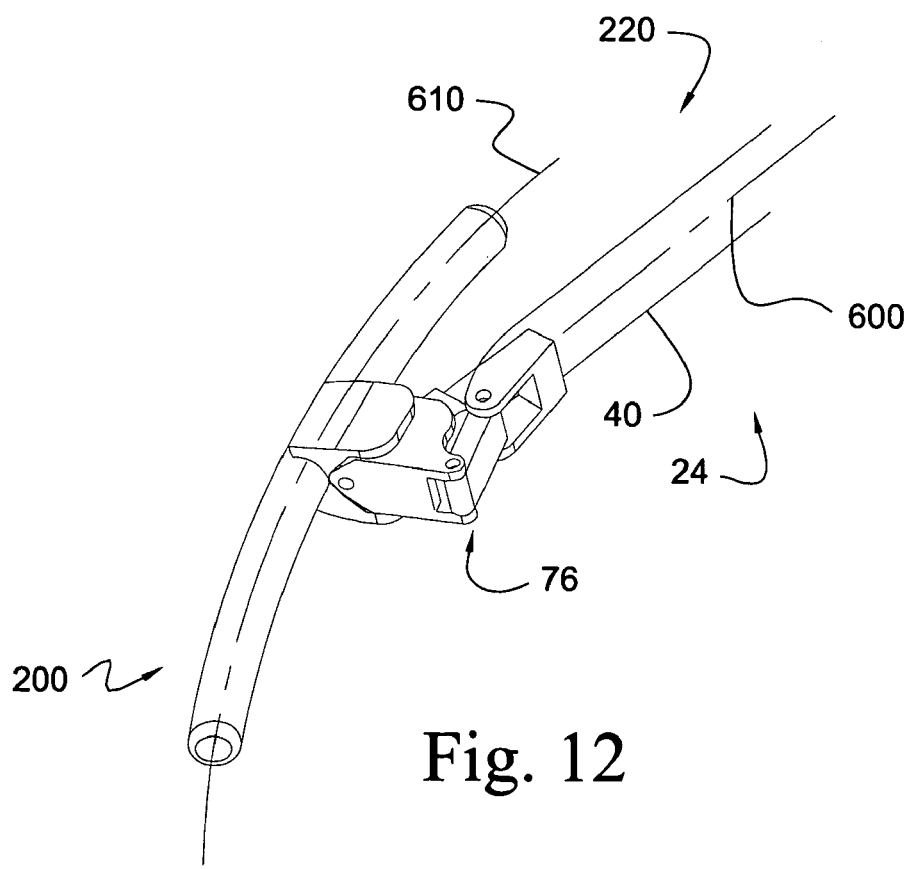
FIG. 12 is an enlarged perspective view of the distal end of the insertion instrument and the implant of FIG. 11.
Figure 13:
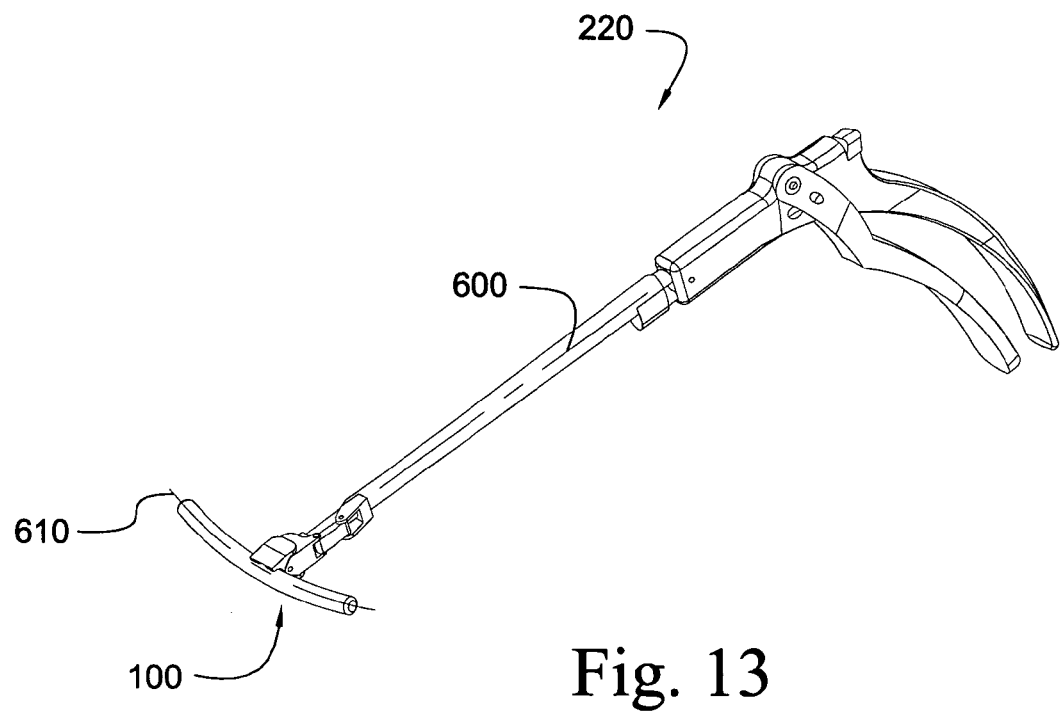
FIG. 13 is a perspective view showing the insertion instrument of FIG. 11 with the implant engaged thereto in an actuated orientation after insertion of the implant to the surgical space in the patient.
Figure 14:
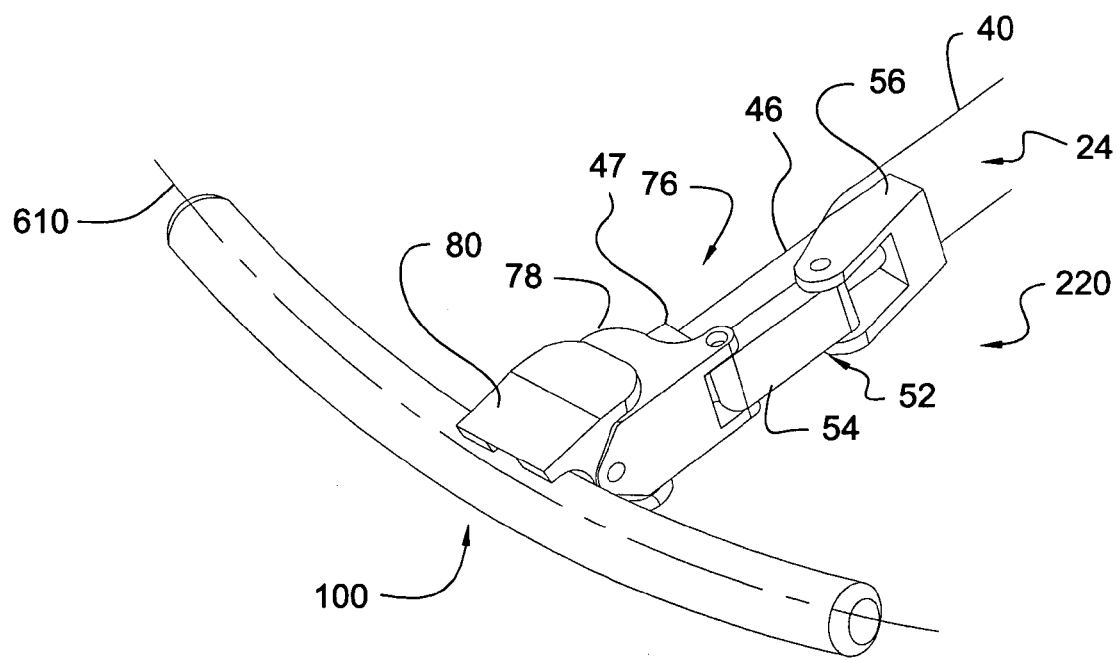
FIG. 14 is an enlarged perspective view of the distal end of the insertion instrument and the implant of FIG. 13.

After insertion through pathway 130, implant 200 can be moved from its low profile insertion orientation to an enlarged profile orientation that allows it to be coupled to anchors, such as spinal hooks, bone screws with an implant receptacle, or other implant engaging member. In FIGS. 12 and 13, handle assembly 22 is manipulated to actuate implant holder 76 through shaft assembly 24 to the enlarged profile orientation with respect to insertion instrument 220. In the second, enlarged profile orientation, longitudinal axis 610 of implant 200 extends transversely with respect to longitudinal axis 600 of shaft assembly 24 and also transversely to the direction of insertion of implant 200. The actuated implant 200 is placed in the desired orientation for engagement of implant 200 at the surgical space.

In the enlarged profile orientation, implant 200 can have a footprint in the implant insertion direction through the pathway that is greater than the transverse dimension defining the opening of the pathway at least adjacent skin level 550. However, when coupled to insertion instrument 220 in the reduced profile orientation, implant 200 can pass through the pathway. Thus, the amount of tissue dissection and retraction required to accommodate insertion of implant 200 is minimized. With implant 200 in the desired position, insertion instrument 220 can be detached from implant 200 and removed from the pathway.

Figure 15:
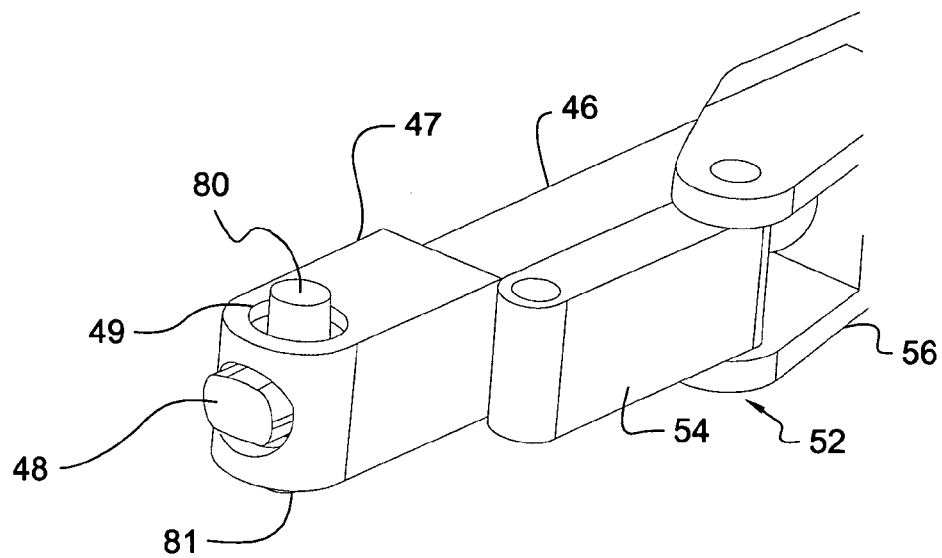
FIG. 15 is a perspective view of the distal end portion of the implant insertion instrument of FIG. 11 with the clamping members and articulating member removed therefrom.

In FIG. 15 there is shown the distal end of shaft assembly 24. Intermediate shaft 46 includes a mounting portion 47 having a hole 49 formed therethrough. An engagement member 80 extends through hole 49, and has an enlarged shoulder (not shown) to retain engagement member 80 in mounting portion 47. A similar second engagement member 81 can be provided through a hole (not shown) on the opposite side of mounting portion 47. Cam member 48, shown in an unlocked position in FIG. 15, extends through mounting portion 47 and is contactable with engagement members 80, 81.

Figure 16:
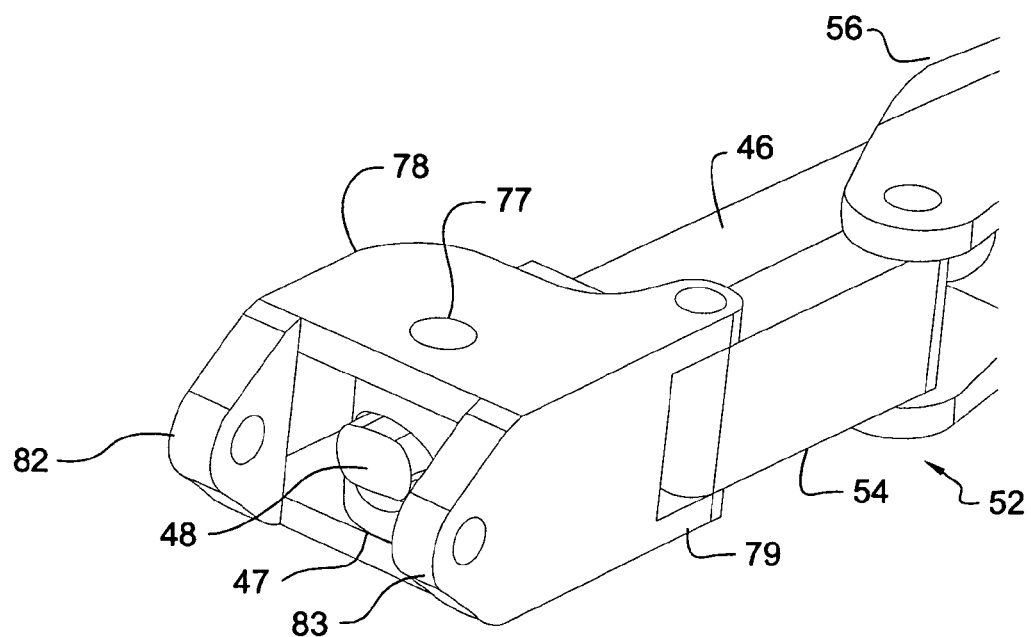
FIG. 16 is a perspective view of the distal end portion of the insertion instrument of FIG. 11 with the clamping members removed therefrom and the cam member in the unlocked position.
Figure 17:
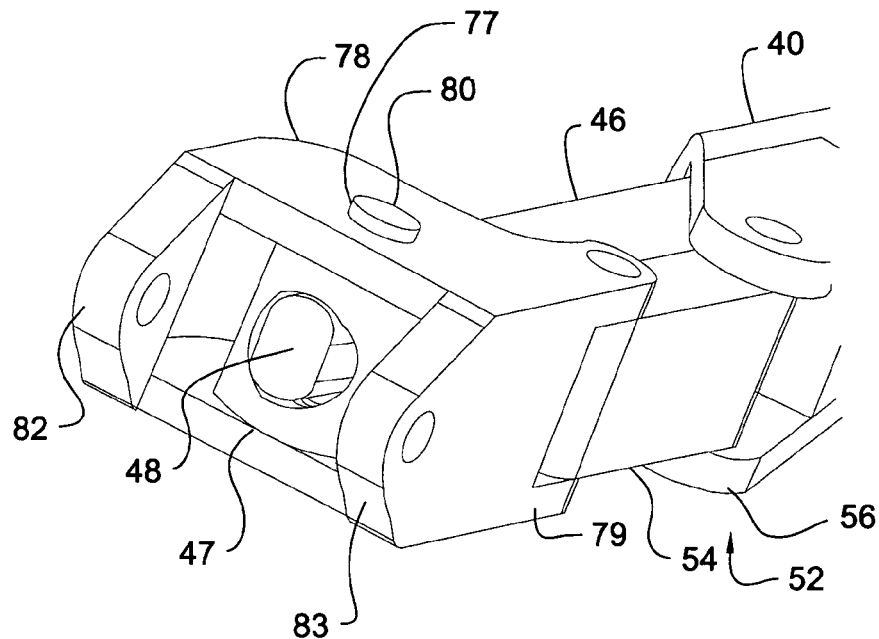
FIG. 17 is a perspective view of the distal end portion of the insertion instrument of FIG. 11 with the clamping members removed therefrom and the cam member in the locked position.

In FIG. 16, an articulating member 78 is pivotally mounted on mounting portion 47. Articulating member 78 includes a bracket 79 pivotally coupled to the distal end of link 54 of linkage mechanism 52. The opposite end of link 54 is pivotally mounted to bracket 56 extending from the distal end of outer shaft 40. Articulating member 78 includes first and second fingers 82, 83 extending distally therefrom. In FIG. 16, cam member 48 (along with lever 50) is in its unlocked position. In FIG. 17, cam member 48 (along with lever 50) has been moved to its locked position, wherein engagement members 80, 81 extend through the holes 77 (only one shown in FIGS. 16, 17) in articulating member 78.

Figure 18:
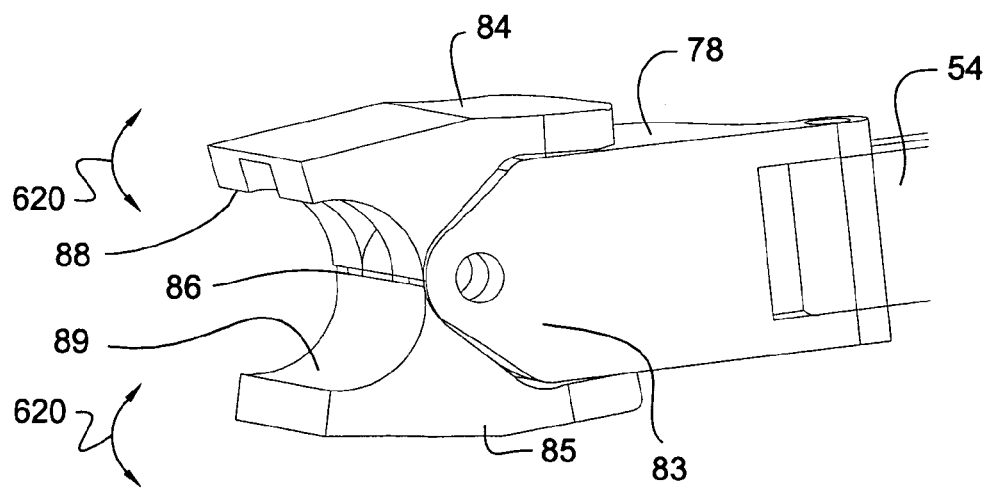
FIG. 18 is a perspective view of the distal end portion of the insertion instrument of FIG. 11 with the clamping members in a disengaged position.
Figure 19:
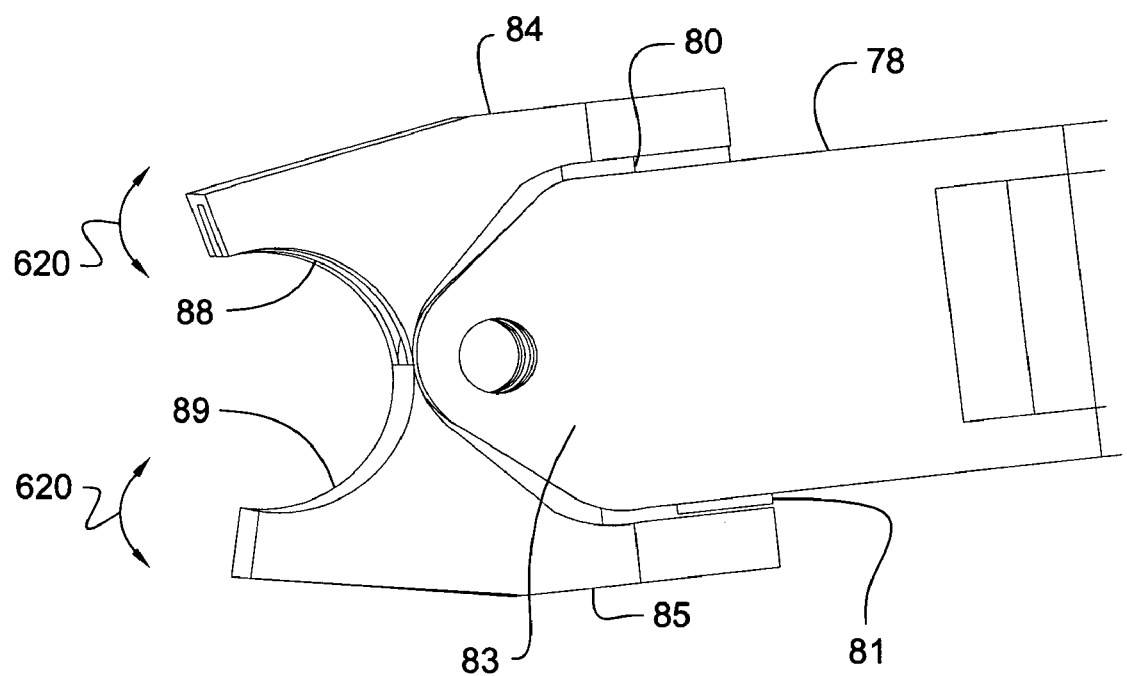
FIG. 19 is a perspective view of the distal end portion of the insertion instrument of FIG. 11 with the clamping members in an engaged position.

In FIG. 18, first and second clamp members 84, 85 are pivotally mounted to fingers 82, 83 of articulating member 78. A hinge 86 can be provided between clamp members 84, 85 for movement of each clamp member either toward each other or away from each other as indicated by arrows 620. Clamping surfaces 88, 89 of respective ones of the clamp members 84, 85 may be moved toward one another to grip the implant by moving cam member 48 to its locked position so that cam member 48 acts on engagement members 80, 81. As shown in FIG. 19, as the engagement members 80, 81 extend through articulating member 78, the engagement members 80, 81 contact the proximal ends of clamp members 84, 85 to move the proximal ends away from one another and move the distal ends of clamp members 84, 85 toward one another.

When cam member 48 is unlocked, engagement members 80, 81 can recess into mounting portion 47. Clamping surfaces 88, 89 of clamp members 84, 85 can move away from one another to release the implant as insertion instrument 220 is withdrawn. Alternatively, cam member 48 and engagement members 80, 81 may be connected, such as by including corresponding gear teeth, so as to positively unlock clamp members 84, 85. Implant 200 can be released in the surgical space in a substantially unconstrained condition, and thereafter constrained or secured as desired. Insertion instrument 220 could also release implant 200 in a constrained condition provided by substantial contact between implant 200 and the anatomy, bone fastener or the like positioned in the surgical space.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A system, comprising
an implant positionable adjacent a surgical space associated with a spinal column of a patient; and
an insertion instrument including an articulating implant holder adjacent a distal end thereof releasably engageable to said implant, wherein said implant is moveable with said implant holder between a reduced profile orientation relative to said insertion instrument and an increased profile orientation relative to said insertion instrument, said implant holder being adapted to release said implant from said implant holder in the increased profile orientation when said implant is positioned adjacent to and substantially unconstrained in the surgical space, wherein said insertion instrument comprises:
an outer shaft coupled and an intermediate shaft extending distally from a proximal handle portion;
said implant holder is pivotally coupled to a distal end of said intermediate shaft; and
a linkage mechanism extends between and pivotally couples said articulating member to said outer shaft.

2. The system of claim 1, wherein said implant is a bone plate.

3. The system of claim 1, wherein said implant is a rod.

4. The system of claim 1, wherein said insertion instrument includes a handle assembly having a distal handle portion pivotally coupled to a proximal handle portion.

5. The system of claim 4, wherein said outer shaft is coupled to said distal handle portion and said intermediate shaft coupled to said proximal handle portion, wherein in said increased profile orientation a distal end of said outer shaft is positioned more proximally relative to said distal end of said intermediate shaft than when in said reduced profile orientation.

6. The system of claim 5, wherein said outer shaft and said intermediate shaft are biased relative to one another so that said implant holder normally assumes said reduced profile orientation.

7. The system of claim 1, wherein said insertion instrument comprises:
a control system;
a connector system extending distally from said control system and including said implant holder pivotally coupled adjacent a distal end thereof; and
a manipulator system associated with said implant holder.

8. The system of claim 1, wherein upon movement of said outer shaft and said inner shaft relative to one another said linkage mechanism causes said articulating member to pivot relative to said intermediate shaft.

9. The system of claim 8, wherein in said reduced profile orientation said linkage mechanism extends transversely to said outer shaft and in said increased profile orientation said linkage mechanism extends generally along said outer shaft.

10. The system of claim 1, wherein said implant includes a receptacle and said implant holder is releasably engageable in said receptacle.

11. The system of claim 10, wherein said implant holder includes an articulating member pivotally mounted adjacent a distal end of said insertion instrument.

12. The system of claim 11, wherein said implant holder further includes a pair of engagement members actuatable from said articulating member to releasably engage said implant in said receptacle.

13. The system of claim 12, wherein said insertion instrument includes a cam member extending therethrough engageable with said pair of opposite engagement members, said cam member moveable from a first position wherein said pair of engagement members are recessed in said articulating member to a second position wherein said cam member biases said pair of engagement members outwardly from said articulating member to releasably engage said implant.

14. The system of claim 11, wherein said articulating member includes a pair of distally extending fingers and a lip extending about a proximal end of said fingers, said lip positionable against a proximal surface of said implant with said pair of fingers positioned in said receptacle.

15. The system of claim 1, wherein said implant holder moves with said implant between said reduced profile orientation and said increased profile orientation.

16. A system, comprising
an implant positionable adjacent a surgical space associated with a spinal column of a patient; and
an insertion instrument including an articulating implant holder adjacent a distal end thereof releasably engageable to said implant, wherein said implant is moveable with said implant holder between a reduced profile orientation relative to said insertion instrument and an increased profile orientation relative to said insertion instrument, said implant holder being adapted to release said implant from said implant holder in the increased profile orientation when said implant is positioned adjacent to and substantially unconstrained in the surgical space, wherein said implant holder includes an articulating member pivotally mounted to a distal end of said insertion instrument and a pair of clamping members mounted along opposite sides of said articulating member, said clamping members being moveable toward one another from a released position wherein said implant is positionable therebetween to an engaged position wherein said pair of clamping members engage said implant therebetween and includes a pair of engagement members actuatable from said articulating member to move said clamping members to said engaged position, wherein said articulating member includes a pair of opposite distally extending fingers and said clamping members extend between and are pivotally coupled to each of said distally extending fingers.

17. The system of claim 16, wherein insertion instrument comprises:
a shaft assembly including an outer shaft and an intermediate shaft extending through said outer shaft;
said articulating member is pivotally mounted to said intermediate shaft; and
a linkage mechanism extending between and pivotally coupled to each of said articulating member and said outer shaft.

18. The system of claim 17, further comprising:
a cam member extending through said intermediate shaft; and
said pair of engagement members in said articulating member being engageable with a distal end of said cam member, said cam member moveable from a first position wherein said pair of engagement members are recessed in said articulating member to a second position wherein said cam member biases said pair of engagement members outwardly from said articulating member into contact with said pair of clamping members to move said pair of clamping members to said engaged position.

19. The system of claim 18, wherein said cam member includes a lever at a proximal end thereof operable to move said cam member between said first position and said second position.

20. The system of claim 17, further comprising a mounting member on a distal end of said intermediate shaft and said articulating member is pivotally mounted to said mounting member.

21. The system of claim 20, wherein said implant holder includes a pair of engagement members movably captured in said mounting member and actuatable from said articulating member to move said clamping members to said engaged position.

22. A system, comprising
an implant positionable adjacent a surgical space associated with a spinal column of a patient; and
an insertion instrument including an articulating implant holder adjacent a distal end thereof releasably engageable to said implant, wherein said implant is moveable with said implant holder between a reduced profile orientation relative to said insertion instrument and an increased profile orientation relative to said insertion instrument, said implant holder being adapted to release said implant from said implant holder in the increased profile orientation when said implant is positioned adjacent to and substantially unconstrained in the surgical space, wherein said implant holder includes an articulating member pivotally mounted to a distal end of said insertion instrument and a pair of clamping members mounted along opposite sides of said articulating member, said clamping members being moveable from a released position wherein said implant is positionable therebetween to an engaged position wherein said pair of clamping members engage said implant therebetween, wherein said articulating member includes a pair of opposite distally extending fingers and said clamping members extend between and are pivotally coupled to each of said distally extending fingers.

23. A system, comprising
an implant positionable adjacent a surgical space associated with a spinal column of a patient; and
an insertion instrument including an articulating implant holder adjacent a distal end thereof releasably engageable to said implant, wherein said implant is moveable with said implant holder between a reduced profile orientation relative to said insertion instrument and an increased profile orientation relative to said insertion instrument, said implant holder being adapted to release said implant from said implant holder in the increased profile orientation when said implant is positioned adjacent to and substantially unconstrained in the surgical space, wherein said implant holder includes an articulating member pivotally mounted to a distal end of said insertion instrument and a pair of clamping members mounted along opposite sides of said articulating member, said clamping members being moveable from a released position wherein said implant is positionable therebetween to an engaged position wherein said pair of clamping members engage said implant therebetween, wherein insertion instrument comprises:
a shaft assembly including an outer shaft and an intermediate shaft extending through said outer shaft;
said articulating member is pivotally mounted to said intermediate shaft; and
a linkage mechanism extending between and pivotally coupled to each of said articulating member and said outer shaft.

24. The system of claim 23, further comprising:
a cam member extending through said intermediate shaft; and
a pair of engagement members in said articulating member engageable with a distal end of said cam member, said cam member moveable from a first position wherein said pair of engagement members are recessed in said articulating member to a second position wherein said cam member biases said pair of engagement members outwardly from said articulating member into contact with said pair of clamping members to move said pair of clamping members to said engaged position.

25. The system of claim 24, wherein said cam member includes a lever at a proximal end thereof operable to move said cam member between said first position and said second position.

26. The system of claim 23, further comprising a mounting member on a distal end of said intermediate shaft and said articulating member is pivotally mounted to said mounting member.

27. The system of claim 26, wherein said implant holder includes a pair of engagement members movably captured in said mounting member and actuatable from said articulating member to move said clamping members to said engaged position.

28. A system, comprising:
an implant positionable adjacent a surgical space associated with a spinal column of a patient; and
an insertion instrument including an articulating implant holder adjacent a distal end thereof releasably engageable to said implant, wherein said implant is moveable with said implant holder between a reduced profile orientation relative to said insertion instrument and an increased profile orientation relative to said insertion instrument, said implant holder being adapted to release said implant from said implant holder in the increased profile orientation when said implant is positioned adjacent to and substantially unconstrained in the surgical space, wherein said insertion instrument includes a handle assembly having a distal handle portion pivotally coupled to a proximal handle portion with a pivot pin and said distal and proximal handle portions are movable toward and way from one another about said pivot pin, wherein said insertion instrument includes an outer shaft coupled to said distal handle portion and an intermediate shaft coupled to said proximal handle portion and said implant holder is pivotally coupled to a distal end of said intermediate shaft, wherein in said increased profile orientation a distal end of said outer shaft is positioned more proximally relative to said distal end of said intermediate shaft than when in said reduced profile orientation, wherein said outer shaft and said intermediate shaft are biased relative to one another so that said implant holder normally assumes said reduced profile orientation and further comprising a linkage mechanism extending between and pivotally coupled to said articulating member to said outer shaft.

29. The system of claim 28, wherein upon movement of said outer shaft and said inner shaft relative to one another said linkage mechanism causes said articulating member to pivot relative to said intermediate shaft.

30. The system of claim 29, wherein in said reduced profile orientation said linkage mechanism extends transversely to said outer shaft and in said increased profile orientation said linkage mechanism extends generally along said outer shaft.

31. The system of claim 28, wherein said implant is a bone plate.

32. The system of claim 28, wherein said implant is a rod.

33. The system of claim 28, wherein said implant holder includes a pair of clamping members actuatable to engage said implant therebetween.

34. A system, comprising
an implant positionable adjacent a surgical space associated with a spinal column of a patient; and
an insertion instrument including an articulating implant holder adjacent a distal end thereof releasably engageable to said implant, wherein said implant is moveable with said implant holder between a reduced profile orientation relative to said insertion instrument and an increased profile orientation relative to said insertion instrument, said implant holder being adapted to release said implant from said implant holder in the increased profile orientation when said implant is positioned adjacent to and substantially unconstrained in the surgical space, wherein said insertion instrument includes a handle assembly having a distal handle portion pivotally coupled to a proximal handle portion with a pivot pin and said distal and proximal handle portions are movable toward and way from one another about said pivot pin, wherein said implant includes a receptacle and said implant holder is releasably engageable in said receptacle, wherein said implant holder includes an articulating member pivotally mounted adjacent a distal end of said insertion instrument, wherein said implant holder further includes a pair of engagement members actuatable from said articulating member to releasably engage said implant in said receptacle, wherein said insertion instrument includes a cam member extending therethrough engageable with said pair of opposite engagement members, said cam member moveable from a first position wherein said pair of engagement members are recessed in said articulating member to a second position wherein said cam member biases said pair of engagement members outwardly from said articulating member to releasably engage said implant.

35. A system, comprising
an implant positionable adjacent a surgical space associated with a spinal column of a patient; and
an insertion instrument including an articulating implant holder adjacent a distal end thereof releasably engageable to said implant, wherein said implant is moveable with said implant holder between a reduced profile orientation relative to said insertion instrument and an increased profile orientation relative to said insertion instrument, said implant holder being adapted to release said implant from said implant holder in the increased profile orientation when said implant is positioned adjacent to and substantially unconstrained in the surgical space, wherein said insertion instrument includes a handle assembly having a distal handle portion pivotally coupled to a proximal handle portion with a pivot pin and said distal and proximal handle portions are movable toward and way from one another about said pivot pin, wherein said implant includes a receptacle and said implant holder is releasably engageable in said receptacle, wherein said implant holder includes an articulating member pivotally mounted adjacent a distal end of said insertion instrument, wherein said articulating member includes a pair of distally extending fingers and a lip extending about a proximal end of said fingers, said lip positionable against a proximal surface of said implant with said pair of fingers positioned in said receptacle.

* * * * *